United States Patent
Ortega et al.

(10) Patent No.: US 12,237,603 B2
(45) Date of Patent: Feb. 25, 2025

(54) SYSTEMS AND METHODS FOR COUPLING ELECTRODES AND ELECTRICAL COMPONENTS

(71) Applicant: Ripple LLC, Salt Lake City, UT (US)

(72) Inventors: Jose Ortega, Murray, UT (US); Alexander Thiessen, Salt Lake City, UT (US); Scott Darold Hiatt, South Jordan, UT (US); Andrew Miller Wilder, Salt Lake City, UT (US)

( * ) Notice: Subject to any disclaimer, the term of this patent is extended or adjusted under 35 U.S.C. 154(b) by 455 days.

(21) Appl. No.: 17/708,061

(22) Filed: Mar. 30, 2022

(65) Prior Publication Data
US 2022/0224030 A1 Jul. 14, 2022

Related U.S. Application Data

(63) Continuation of application No. PCT/US2020/054941, filed on Oct. 9, 2020.
(Continued)

(51) Int. Cl.
  *H01R 4/48* (2006.01)
  *H01R 12/72* (2011.01)
(Continued)

(52) U.S. Cl.
  CPC ......... *H01R 12/722* (2013.01); *H01R 13/501* (2013.01); *H01R 13/6658* (2013.01); *H05K 1/181* (2013.01)

(58) Field of Classification Search
  CPC ............... H01R 12/722; H01R 13/501; H01R 13/6658; H05K 1/181; A61B 5/293; A61B 5/296; A61B 5/273
  See application file for complete search history.

(56) References Cited

U.S. PATENT DOCUMENTS 4,653,501 A 3/1987 Cartmell
5,341,806 A 8/1994 Gadsby
(Continued)

FOREIGN PATENT DOCUMENTS

WO 2021072164 A1 4/2021

OTHER PUBLICATIONS

International Patent Application PCT/US2020/054941, International Search Report and Written Opinion mailed Jan. 22, 2021, 7pp.

*Primary Examiner* — Abdullah A Riyami
*Assistant Examiner* — Nelson R. Burgos-Guntin
(74) *Attorney, Agent, or Firm* — Jared Cherry

(57) ABSTRACT

Disclosed herein are systems and methods for coupling electrodes to electrical components that may be utilized in a variety of applications to collect data from the electrodes. In one embodiment, an electrode connection system to couple an electrode to an electrical component. The electrode connection system includes the electrical connector body comprising a PCB assembly cavity and an electrode channel. An electrode clamp coupled to the electrical connector body may include an engaging mechanism and at least one electrode clamp pad protrusion to couple an at least one electrode pad to an at least one connector pad. The PCB assembly may include at least one connector pad. The electrode may comprise at least one electrically active electrode pad. The electrical component may collect data from the electrode or stimulate tissue utilizing the electrode.

12 Claims, 10 Drawing Sheets

Related U.S. Application Data

(60) Provisional application No. 62/913,601, filed on Oct. 10, 2019.

(51) Int. Cl.
    *H01R 13/50*     (2006.01)
    *H01R 13/66*     (2006.01)
    *H05K 1/18*      (2006.01)

(56) References Cited

U.S. PATENT DOCUMENTS

| | | | | |
|---|---|---|---|---|
| 5,341,812 | A * | 8/1994 | Allaire | H01R 31/06 |
| | | | | 600/508 |
| 6,594,515 | B2 * | 7/2003 | Watson | A61B 5/4362 |
| | | | | 600/376 |
| 6,623,312 | B2 * | 9/2003 | Merry | A61B 5/308 |
| | | | | 439/91 |
| 7,618,377 | B2 * | 11/2009 | McAtamney | A61B 5/301 |
| | | | | 600/300 |
| 9,486,280 | B2 * | 11/2016 | Koblish | A61B 18/1206 |
| 9,775,536 | B2 * | 10/2017 | Felix | A61B 5/273 |
| 9,787,022 | B2 * | 10/2017 | Wilcox | H01R 13/6658 |
| 10,736,529 | B2 * | 8/2020 | Bardy | A61B 5/0022 |
| 2008/0132773 | A1 | 6/2008 | Burnes | |
| 2008/0249390 | A1 | 10/2008 | McIntire | |
| 2013/0165924 | A1 * | 6/2013 | Mathur | A61B 18/16 |
| | | | | 606/41 |
| 2020/0000407 | A1 * | 1/2020 | Pacholik | A61B 5/274 |
| 2021/0196334 | A1 * | 7/2021 | Sarley | A61B 17/320092 |
| 2021/0196335 | A1 * | 7/2021 | Messerly | A61B 18/00 |
| 2023/0231330 | A1 * | 7/2023 | West | A61B 5/28 |
| | | | | 439/476.1 |

\* cited by examiner

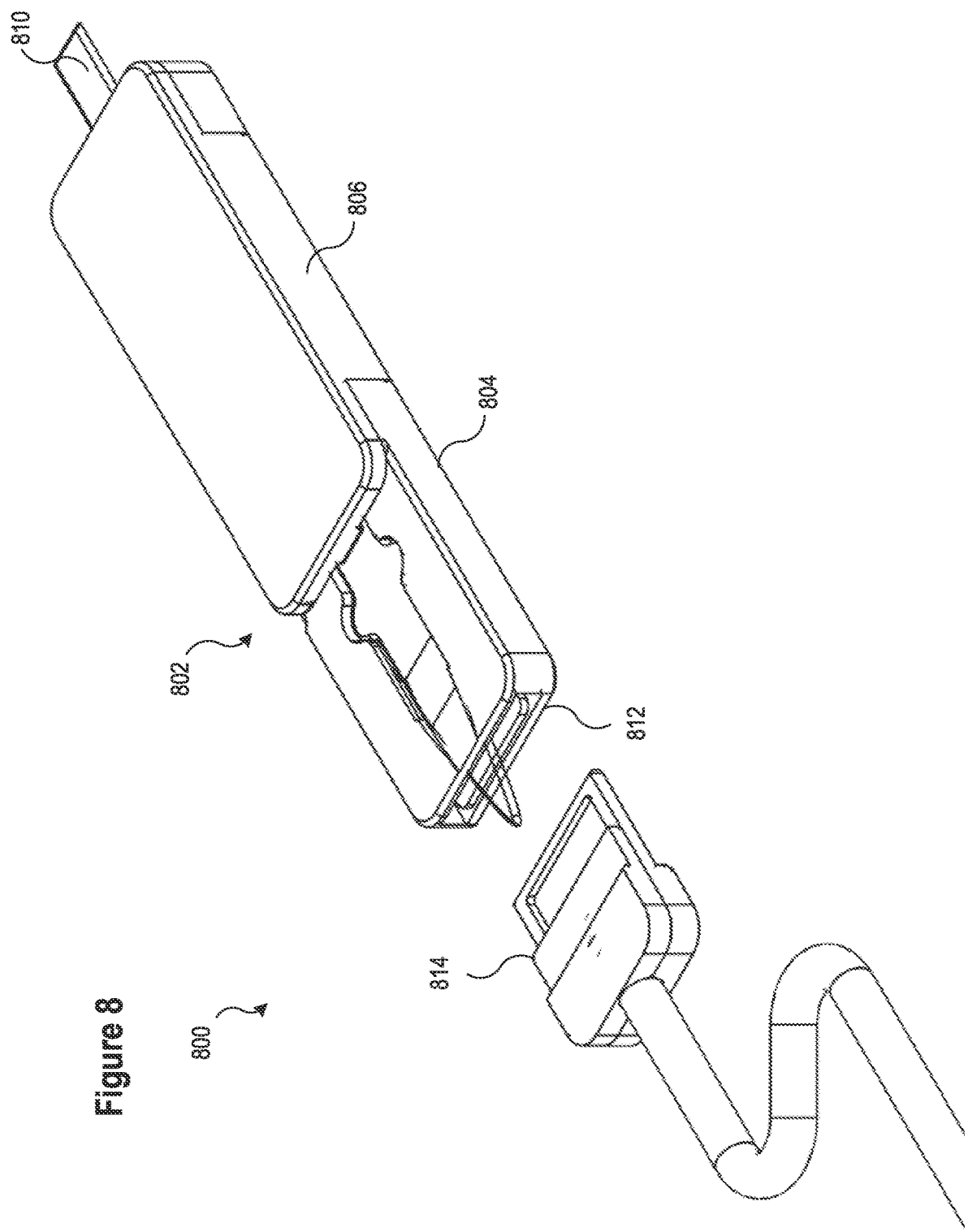

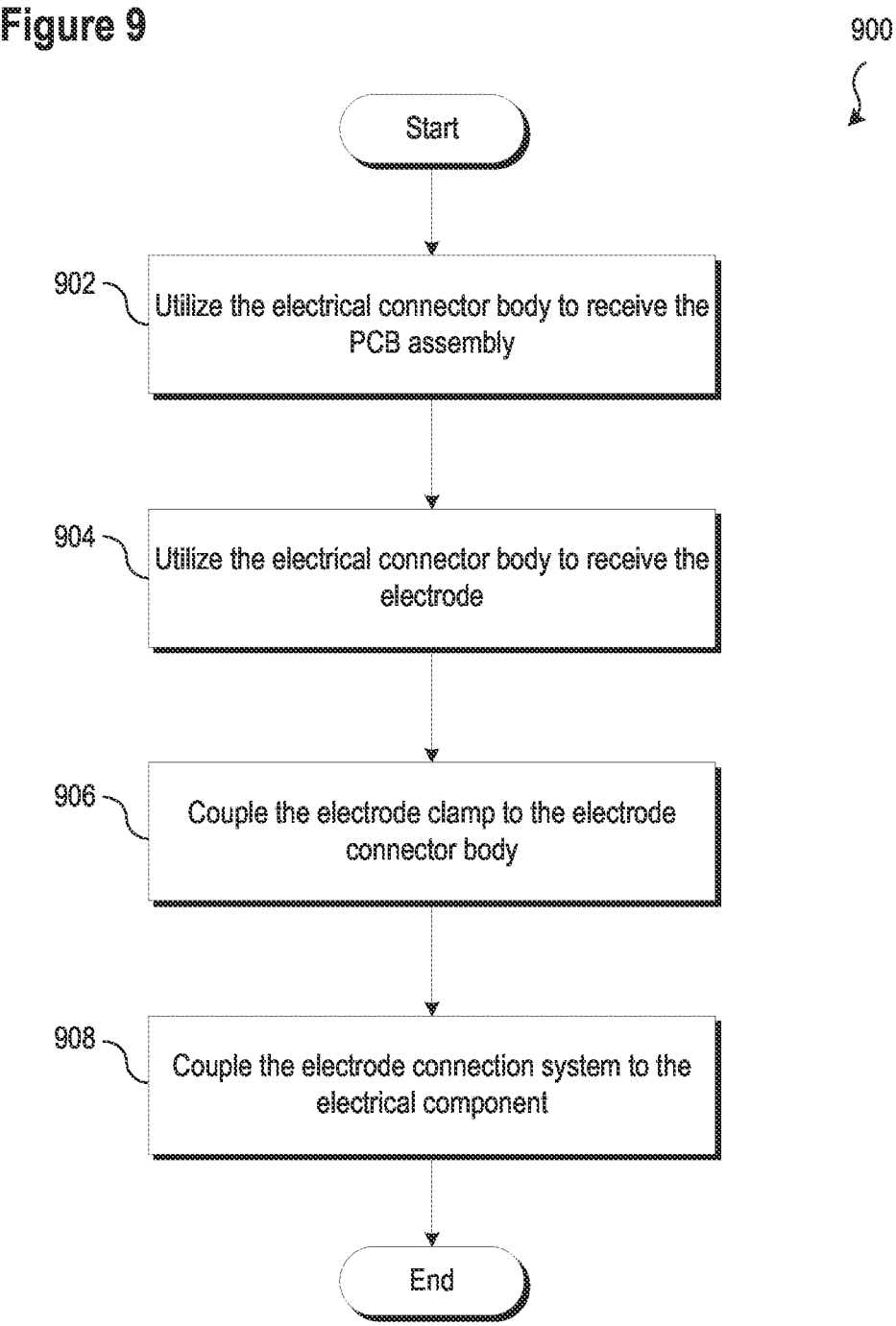

SYSTEMS AND METHODS FOR COUPLING ELECTRODES AND ELECTRICAL COMPONENTS

RELATED APPLICATIONS

This application is a continuation of PCT International Patent Application No. PCT/US2020/054941, filed Oct. 9, 2020 and titled "Systems and Methods for Coupling Electrodes and Electrical Components," which claims the benefit of the filing date of U.S. Patent Application No. 62/913,601, filed Oct. 10, 2019, and titled "Systems and Methods for Coupling Electrodes and Electrical Components," both of which are hereby incorporated by reference in their entireties.

BRIEF DESCRIPTION OF THE DRAWINGS

FIG. 8 illustrates a perspective view of a system wherein the electrode connector system is not coupled to the electrical component consistent with embodiments of the present disclosure.

FIG. 9 illustrates a flow chart of a method of coupling an electrode and electrical components consistent with embodiments of the present disclosure.

DETAILED DESCRIPTION OF PREFERRED EMBODIMENTS

Disclosed herein are systems and methods for coupling electrodes to electrical components that may be utilized in a variety of applications to collect data from the electrodes and/or to transmit signals via the electrodes. In certain embodiments, an electrical connector system may be used to couple an electrode to an electrical component including an electric connector, a card edge contact, or another electrical component. The electrode may be utilized to collect data from a variety of sources including the surface of a patient's brain, spinal column, other surfaces of the body, muscle tissue, or other electrically active elements.

The electrode may comprise two ends: one end may be utilized to record and/or stimulate a target area, and the other end may be utilized to connect to the electrical component. A first end of the electrode may be utilized to interface with a bioelectrically active target area, such as the surface of the brain, and may be used to receive bioelectric signals. A second end of the electrode may be utilized to connect to the electrical component and may transmit the signals received from the surface of the brain, or other target area, to the electrical component. By coupling the electrode to the electrical component, data received by the electrode may be collected by the electrical component and used to monitor electrical signals in the surface on which the electrode is disposed, such as a patient's brain. In addition, signals may be transmitted via the electrode to stimulate the target area.

The present disclosure includes various embodiments utilizing the electrical connector system to couple the electrode to the electrical component. The systems and methods disclosed herein may provide a simple and reliable connection between the electrode and a variety of other devices, including monitoring systems. Such monitoring systems may include systems for monitoring and analyzing neurological signals in animals and humans. An inability to connect, disconnect, and reconnect electrodes and electrical components provides challenges in the ability to collect data. Without the ability to collect data read by the electrodes in an easy, reliable, and practical manner, the data may be useless.

Figure 1:
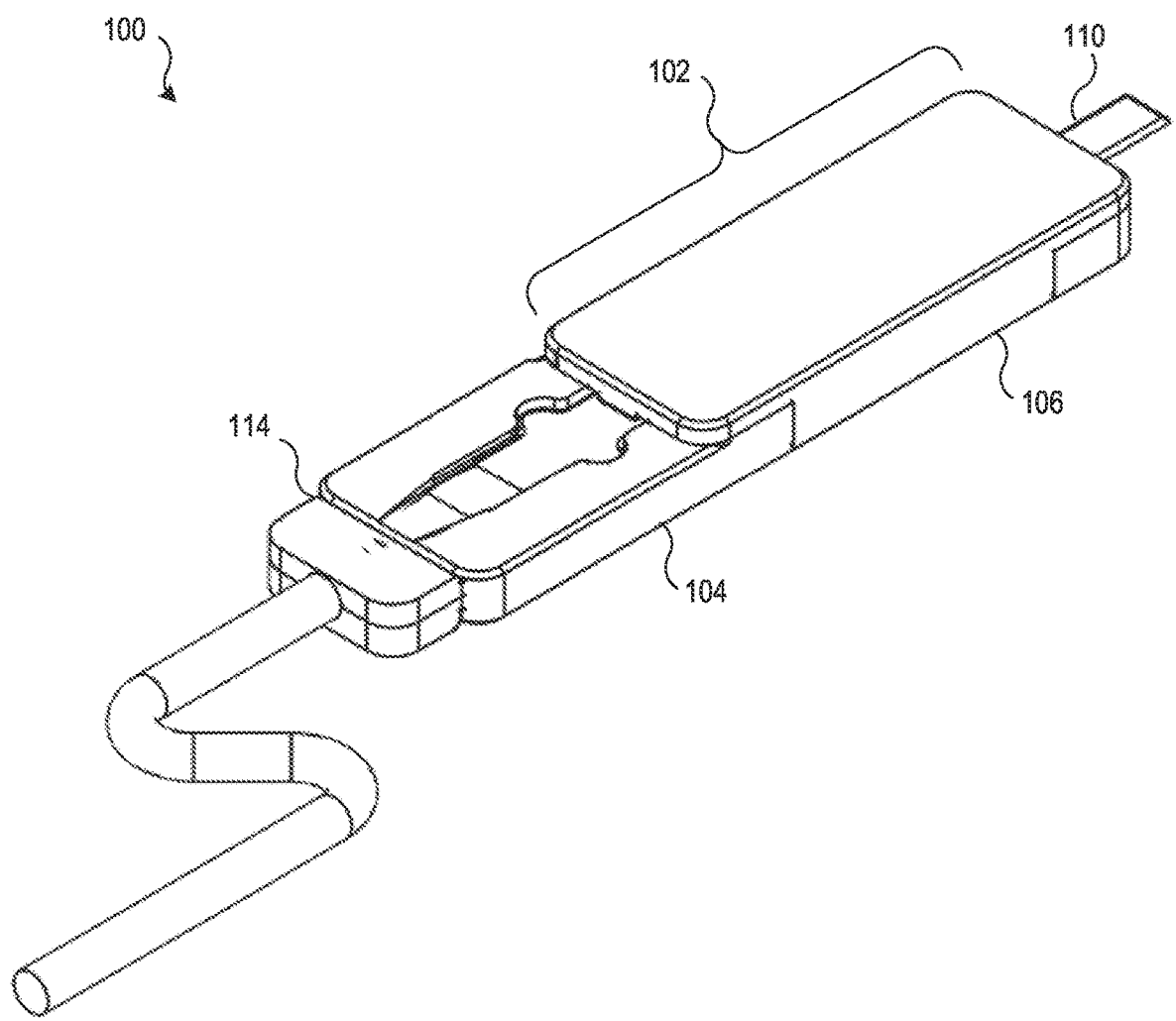
FIG. 1 illustrates a perspective view of an electrical connector system consistent with embodiments of the present disclosure.

FIG. 1 illustrates a perspective view of an electrical connector system 100 consistent with embodiments of the present disclosure. The electrical connector system 100 may include an electrode connection system 102, an electrical connector body 104, an electrode clamp 106, an electrode 110, and an electrical connection 114. A PCB assembly (not shown) disposed within the electrical connector body 104 may be in electrical communication with the electrode 110. The electrode connection system 102 allows the electrical connection 114 to collect data from the electrode 110 via the electrical connection 114. The data may be transmitted via the electrical connector system 100 to a system for recording bioelectric signals (not shown). Further, the system may also generate bioelectrical signals that are transmitted via the electrical connector system 100 and used to stimulate a target area.

The electrode connection system 102 is utilized to stabilize the electrode 110 and allow the electrical connection 114 to receive data from the electrode 110. The electrode 110 may be comprised of two ends: a first end to receive data from and/or stimulate a target area, and a second end to connect to the electrical connection 114. A first plurality of electrically active electrode pads (not shown) may be disposed on the first end of the electrode to receive bioelectrical signals from a target area, and a second plurality of electrically active electrode pads may be disposed on the second end of the electrode and be in electrical communication with the electrical connection 114.

The electrical connector body 104 may receive the PCB assembly and the electrode 110. In some embodiments, the electrode clamp 106 may secure the electrode 110 within the electrical connector body 104. The electrical connection 114 may be selectively coupled to the electrode connection system 102. In some embodiments, the electrical connector system 100 may include the electrical connection 114 coupled to the PCB assembly. In these embodiments, the data received by the electrode 110 may be transmitted via the electrical connection 114.

Figure 2A:
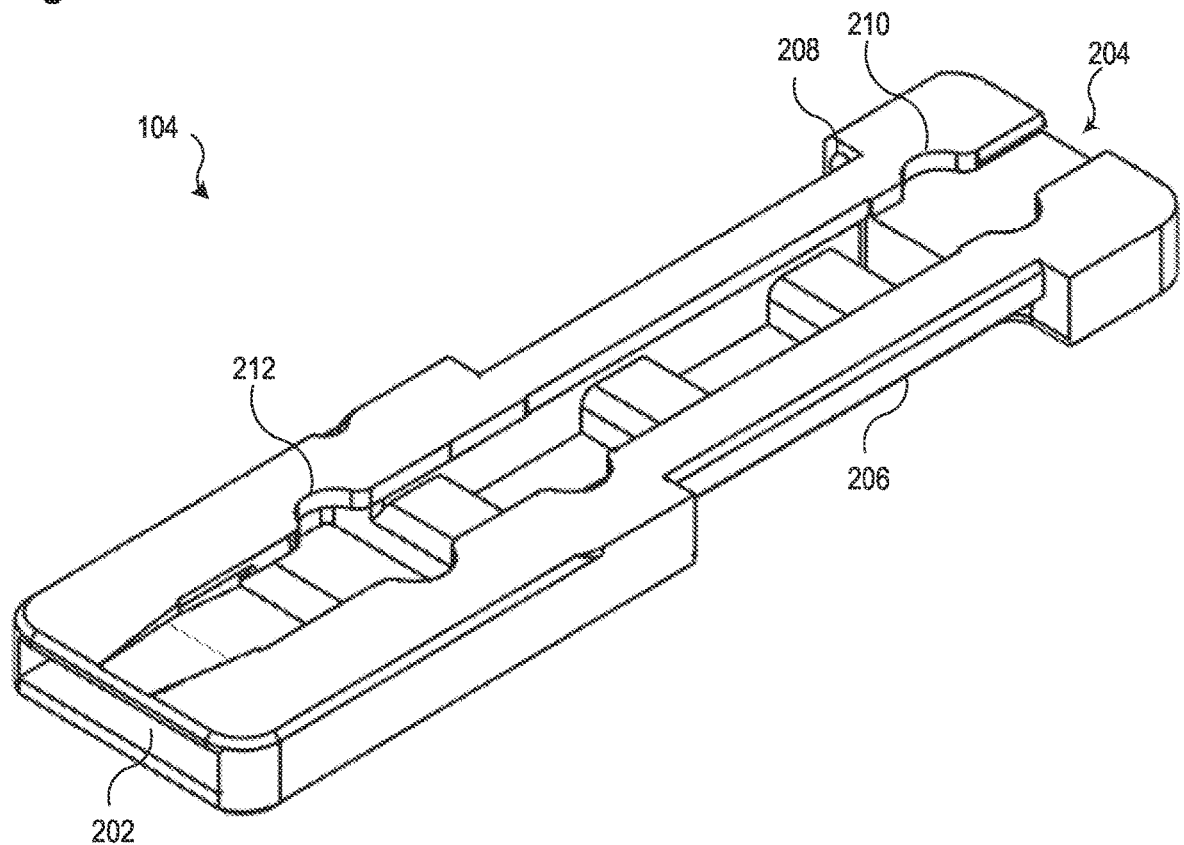
FIG. 2A illustrates a perspective view of an electrical connector body consistent with embodiments of the present disclosure.

FIG. 2A illustrates a perspective view of the electrical connector body 104 consistent with the embodiments of the present disclosure. The electrical connector body 104 may include a PCB assembly cavity 202 and an electrode channel 204. The PCB assembly cavity 202 may receive a PCB assembly (not shown). In some embodiments, the PCB assembly cavity 202 may hold the PCB assembly. The electrode channel 204 may receive an electrode (not shown). In some embodiments, the electrode channel 204 may hold the electrode. The electrical connector body 104 may receive a PCB assembly and an electrode. In some embodiments, the PCB assembly is coupled to the electrode within the electrical connector body 104.

In some embodiments, the electrode clamp (e.g., electrode clamp 106 illustrated in FIG. 1) may be connected to the electrical connector body 104 using a hinge created by a hinge protrusion 208 and a corresponding indentation on the electrode clamp. The hinge protrusion 208 and a corresponding indentation on the electrode clamp may allow the electrode clamp to be opened to receive an electrode and closed to secure the electrode within the electrode channel 204. In other embodiments, a hinge may be formed in other ways.

In some embodiments, the electrode clamp engages with an engaging mechanism 206 in a closed position. The engaging mechanism 206 may permit the electrode clamp to secure an electrode within the electrode channel 204 in a closed position, while also allowing the electrode clamp 106 to be opened and permitting the electrode to be removed from the electrode channel 204.

In various embodiments, the electrode channel 204 may be shaped to receive an electrode having a corresponding shape. In the illustrated embodiment, a plurality of alignment indicators 210, 212 may accommodate corresponding features of the electrode. Such features may be used to place the electrode in electrode channel 204 at the appropriate location to align electrical contacts of the electrode and the PCB assembly.

Figure 2B:
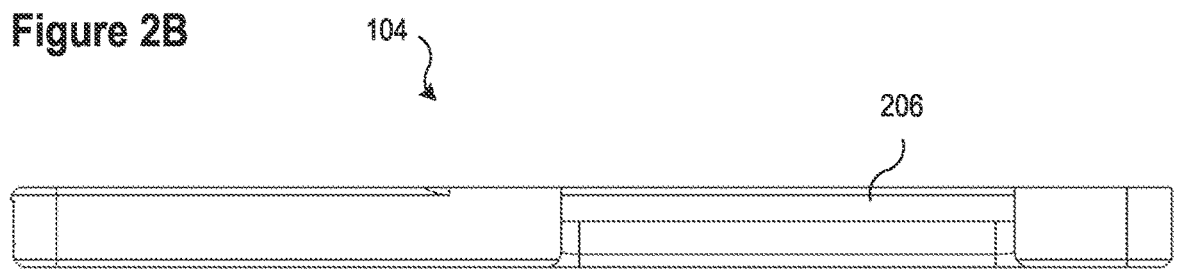
FIG. 2B illustrates a side view of the electrical connector body consistent with embodiments of the present disclosure.

FIG. 2B illustrates a side view of the electrical connector body 104 consistent with embodiments of the present disclosure. In some embodiments, the engaging mechanism 206 may be a snap lock. The engaging mechanism 206 may comprise a ridge onto which a locking mechanism disposed on the electrical connector may clamp.

Figure 3A:
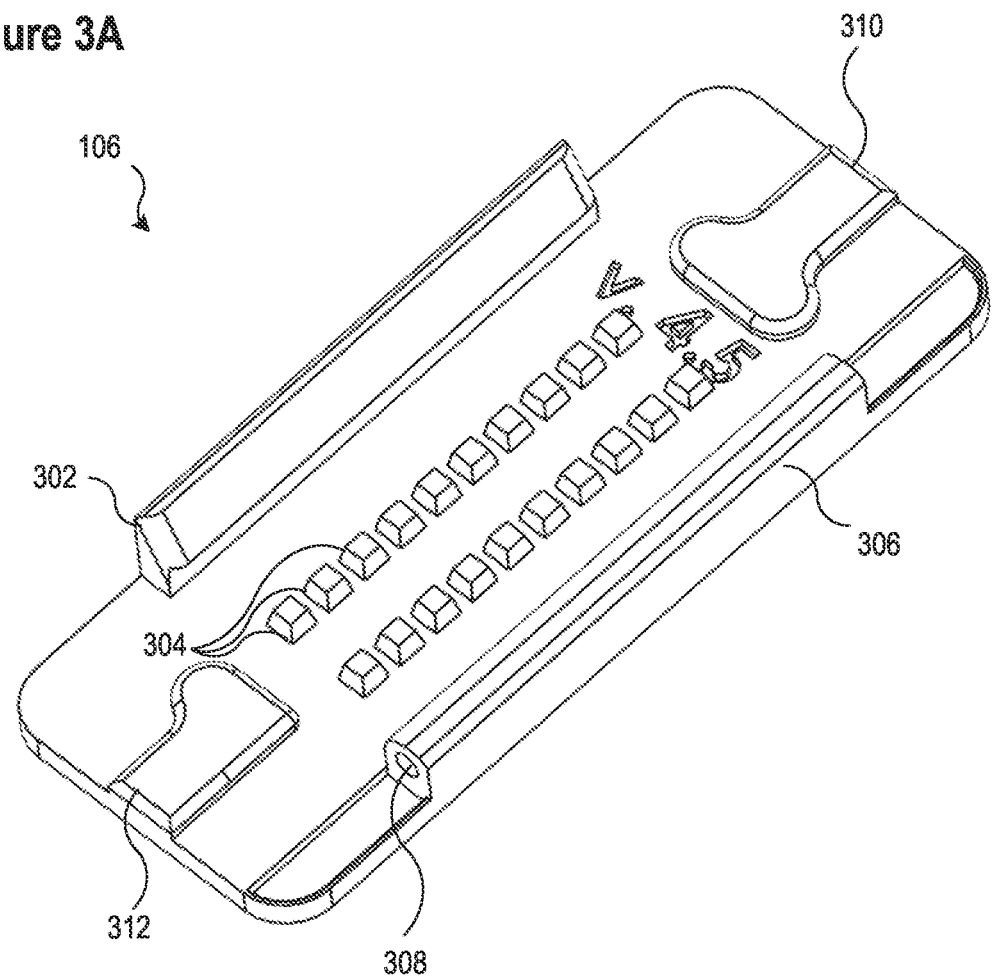
FIG. 3A illustrates a perspective view of an electrode clamp consistent with embodiments of the present disclosure.

FIG. 3A illustrates a perspective view of the electrode clamp 106 consistent with embodiments of the present disclosure. In the illustrated embodiment, a hinge 306 may rotatably couple to the electrical connector body (illustrated in FIG. 2B) using the hinge protrusion (illustrated in FIG. 2A) and a hinge dimple 308. In alternative embodiments, other types of hinges or connectors may be utilized to secure the electrode (not shown) within the electrode channel (illustrated in FIG. 2A). For example, in one embodiment, a hinge may be formed using a deformable connection between a first portion of the electrode clamp 106 (e.g., the portion illustrated in FIG. 3A) and a second portion of the electrode clamp 106 (e.g., the portion illustrated in FIG. 3C).

A plurality of protrusions 304 may be disposed along the electrode clamp 106 at locations that correspond to points of electrical connection between the electrode and the PCB assembly. The protrusions 304 may be formed at a predetermined height to create a reliable electrical connection between the electrode and the PCB assembly. A plurality of electrode channel feature protrusions 310, 312 may be used to position the electrode within the electrode channel and at the appropriate height with respect to the PCB assembly. The channel feature protrusions 310, 312 may help to maintain an electrode in place and to prevent movement of the electrode with respect to the electrode clamp 106 when the electrode clamp 106 is closed.

The electrode clamp 106 may include a locking mechanism 302 and at least one protrusion 304. In some embodiments, the electrode clamp 106 is pivotally connected to the electrical connector body using hinge 306. The locking mechanism 302 is utilized to couple the electrode clamp 106 to the electrical connector body in a closed position. In some embodiments, an engaging mechanism (such as engaging mechanism 206 illustrated in FIG. 2A) engages with locking mechanism 302 to couple the electrode clamp 106 to the electrical connector body in the closed position. Coupling the electrical connector body to the electrode clamp 106 allows the PCB assembly and the electrode to be secured in the electrical connector body. In some embodiments, the locking mechanism 302 may be a snap lock.

Figure 3B:
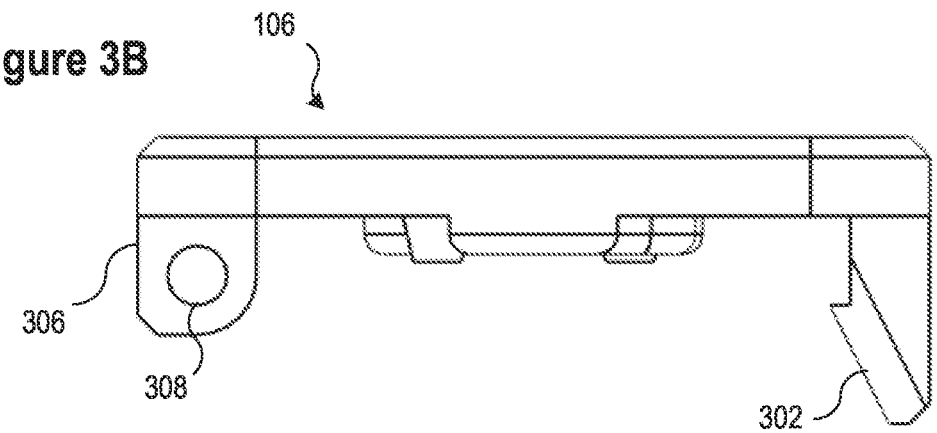
FIG. 3B illustrates a front view of the electrode clamp consistent with embodiments of the present disclosure.

FIG. 3B illustrates a front view of the electrode connector clamp 106 consistent with embodiments of the present disclosure. In the illustrated embodiment, the electrode connector clamp 106 includes the locking mechanism 302. The locking mechanism 302 is received by the engaging mechanism. Utilizing the locking mechanism 302 to couple to the engaging mechanism allows the electrode to be secured in the electrode channel. In some embodiments, the locking mechanism 302 is a snap lock. The snap lock is received by the engaging mechanism to allow the electrode clamp 106 to be coupled to the electrical connector body.

Figure 3C:
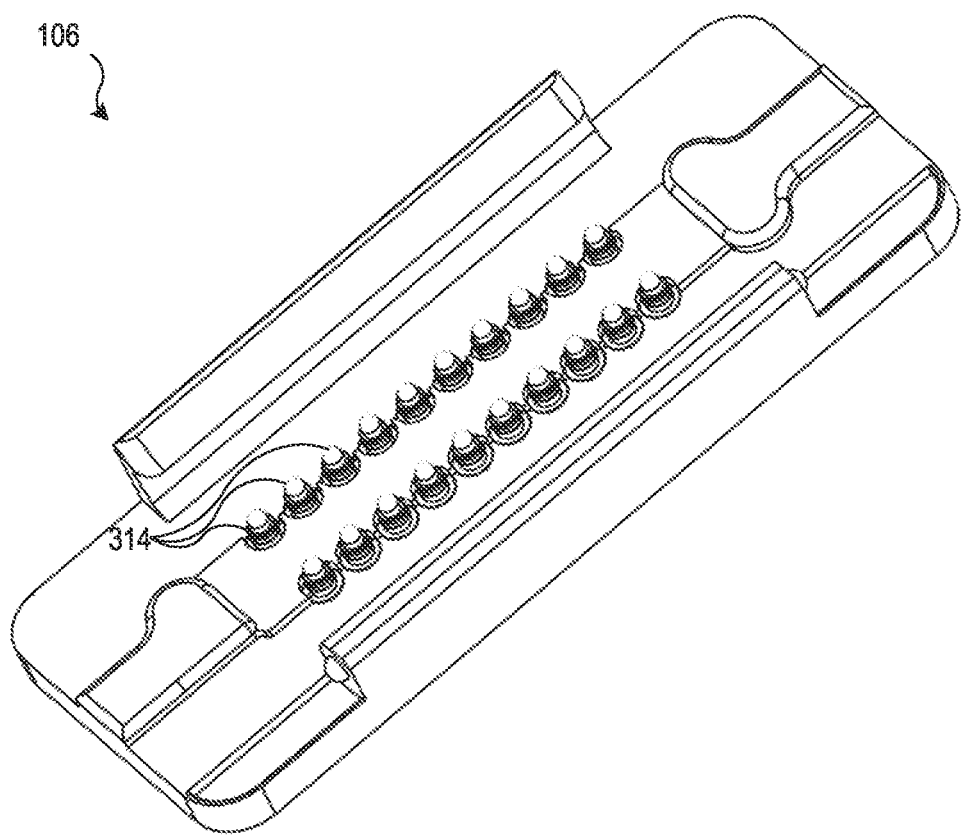
FIG. 3C illustrates a perspective view of an electrode clamp comprising a plurality of metal dowels to make electrical contact between an electrode and a printed circuit board ("PCB") consistent with embodiments of the present disclosure.

FIG. 3C illustrates a perspective view of the electrode clamp 106 in which the protrusions 304 are aligned with a corresponding plurality of metal dowels 314 consistent with embodiments of the present disclosure. In some embodiments, protrusions 304 are formed by inserting metal dowels 314 through openings in the electrode clamp 106. In the illustrated embodiment, the electrode clamp 106 comprises openings to receive the metal dowels 314. The openings in the electrode clamp 106 are utilized to allow the metal dowels 314 to create a connection between the PCB assembly and the electrode. The metal dowels 314 may be utilized to hold the PCB assembly and the electrode in place and form a connection between the PCB assembly and the electrode. The metal dowels 314 may be inserted through the openings in the electrode clamp 106 to form the protrusions 304.

Figure 4:
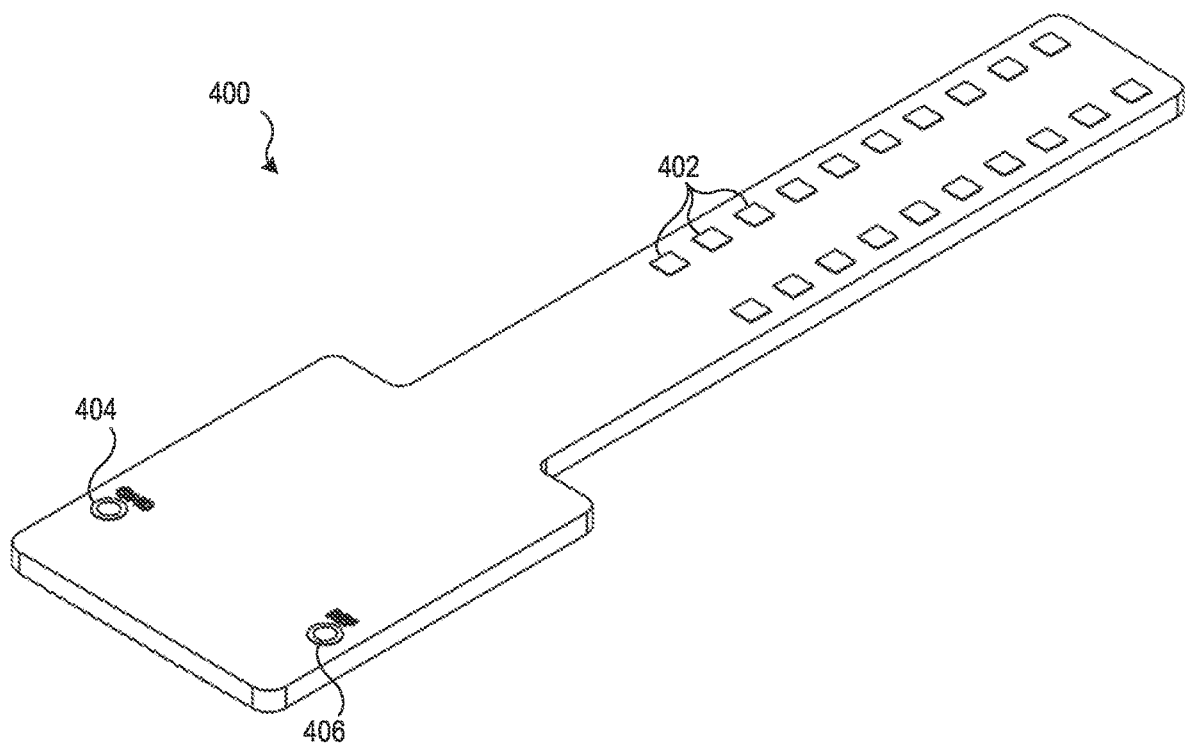
FIG. 4 illustrates a view of a PCB assembly consistent with embodiments of the present disclosure.

FIG. 4 illustrates a view of the PCB assembly 400 consistent with embodiments of the present disclosure. The PCB assembly 400 may include a plurality of connector pads 402. The connector pads 402 may be disposed at points of electrical connection between the electrode (not shown) and the PCB assembly 400. The connector pads 402 may receive signals from the electrode, or the connector pads 402 may transmit signals to the electrode. In some embodiments, the PCB assembly 400 may include electrical connectors 404, 406 to couple to other systems, such as recording or stimulation systems. In some embodiments, the PCB assembly 400 may include card edge contacts to couple to an electrical component (not shown).

As may be appreciated from FIG. 3A, FIG. 3C, and FIG. 4, the protrusions 304 (illustrated in FIG. 3A) and the metal dowels 314 (illustrated in FIG. 3C) may align with the connector pads 402. The protrusions 304 may press an electrically active area of the electrode into contact with the metal dowels 314, which may in turn make an electrical connection between the electrode and PCB assembly 400.

The PCB assembly 400 may provide an electrical interface between the electrode and other systems (e.g., recording or stimulation systems); however, other types of interfaces may be used in other embodiments. For example, the metal dowels 314 (illustrated in FIG. 3C) may be coupled to wires that may connect to such systems. In various embodiments, the wires may be coupled to other systems using a standardized or proprietary cable or interface.

Figure 5:
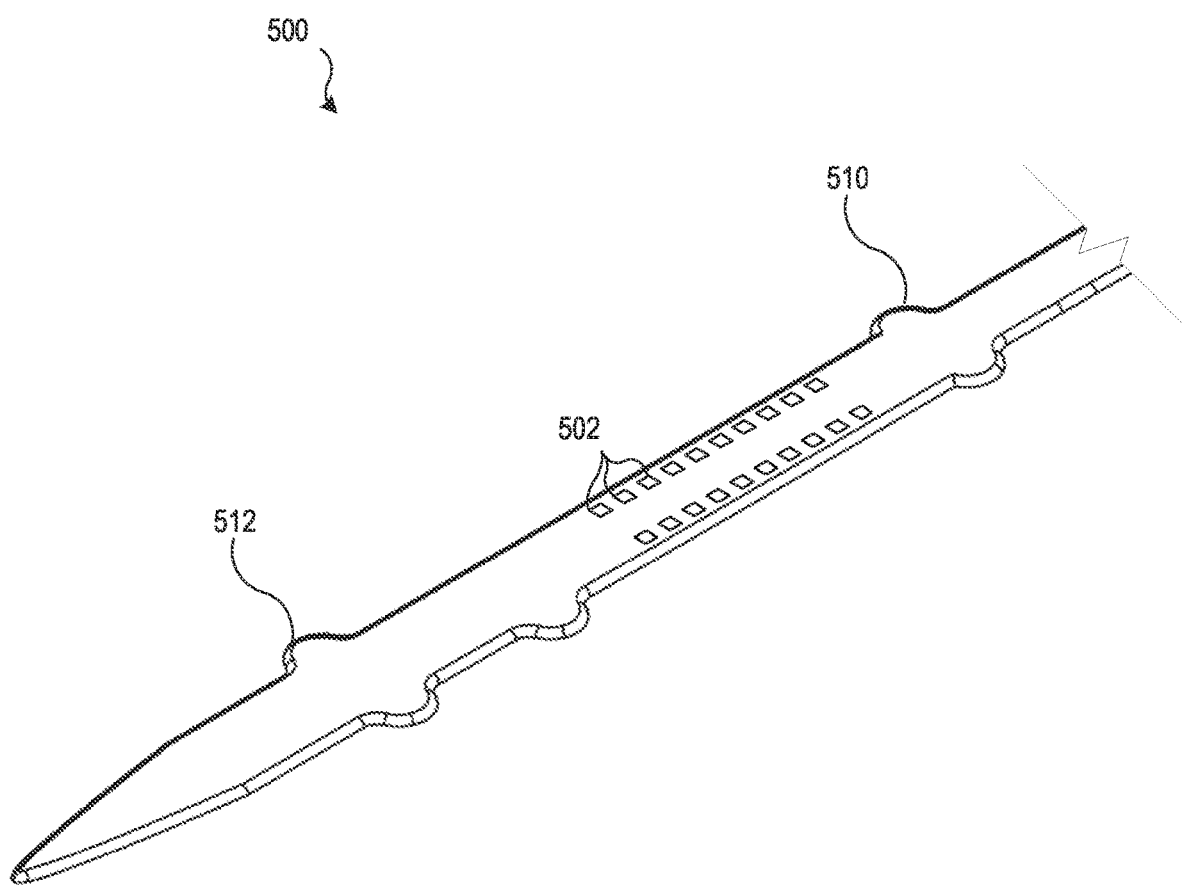
FIG. 5 illustrates a view of an electrode consistent with embodiments of the present disclosure.

FIG. 5 illustrates a view of the electrode 500 consistent with embodiments of the present disclosure. In the illustrated embodiment, electrode 500 includes a plurality of electrically active electrode pads 502 disposed at an end and suitable for use with various embodiments of the electrical connector systems disclosed herein. The opposite end of the electrode 500 may also include a plurality of electrically active electrode pads 502 that may interface with a target area (e.g., a patient's brain or other bioelectrically active area). The plurality of electrically active electrode pads on each end of the electrode may be in electrical communication via conductive paths through the electrode 500.

In some embodiments, the electrode pads 502 may be electrically coupled to one or more connector pads, such as the connector pads 402 in FIG. 4 on a PCB assembly 400. Further, the electrode pads 502 may come into contact with electrical conductors (e.g., the metal dowels 314 illustrated in FIG. 3C) to collect electrical signals from or transmit electrical signals to the electrode 500.

In some embodiments, the electrode 500 may be formed of a flexible material. In some embodiments, the electrode 500 may comprise a flat end tail. In some embodiments, the electrode 500 may comprise a round end tail. In some embodiments, the electrode 500 may comprise two ends, wherein one end is utilized to connect to a target area to gather data and/or stimulate the area and the other end is utilized for transmitting data to an electrical component. The portion of electrode 500 illustrated in FIG. 5 may be utilized for transmitting data to an electrical component. In some embodiments, the tail end of the electrode 500 is utilized to connect with the target area. In certain embodiments, the electrode 500 may comprise one or more of the electrodes disclosed in U.S. Pat. No. 9,061,134 and available from Ripple, LLC, of Salt Lake City, Utah.

Electrode 500 may include alignment features 510, 512 that may be used to align and secure electrode 500 within an electrode channel, such as electrode channel 204 illustrated in FIG. 2A. Alignment features 510, 512 may be placed within corresponding electrode channel features, such as alignment indicators 210, 212 illustrated in FIG. 2A.

Figure 6:
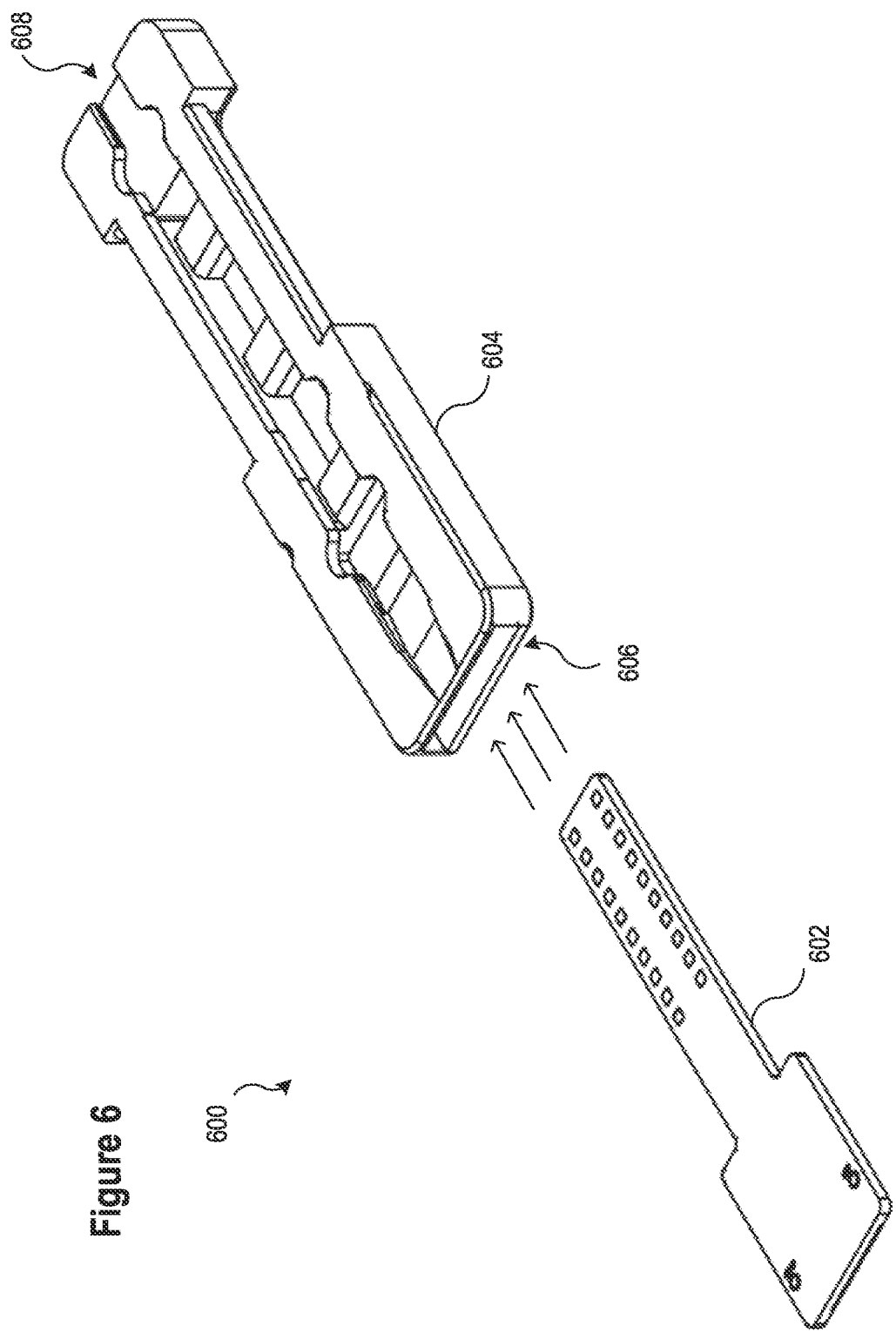
FIG. 6 illustrates a perspective view illustrating insertion of a PCB assembly into an electrical connector body consistent with embodiments of the present disclosure.

FIG. 6 illustrates a perspective view 600 illustrating insertion of a PCB assembly 602 into an electrical connector body 604 consistent with embodiments of the present disclosure. In some embodiments, the electrical connector body 604 receives the PCB assembly 602 within a PCB assembly cavity 606. The electrical connector body 604 may facilitate contact between the PCB assembly 602 and an electrode (not shown) placed within an electrode channel 608.

Figure 7:
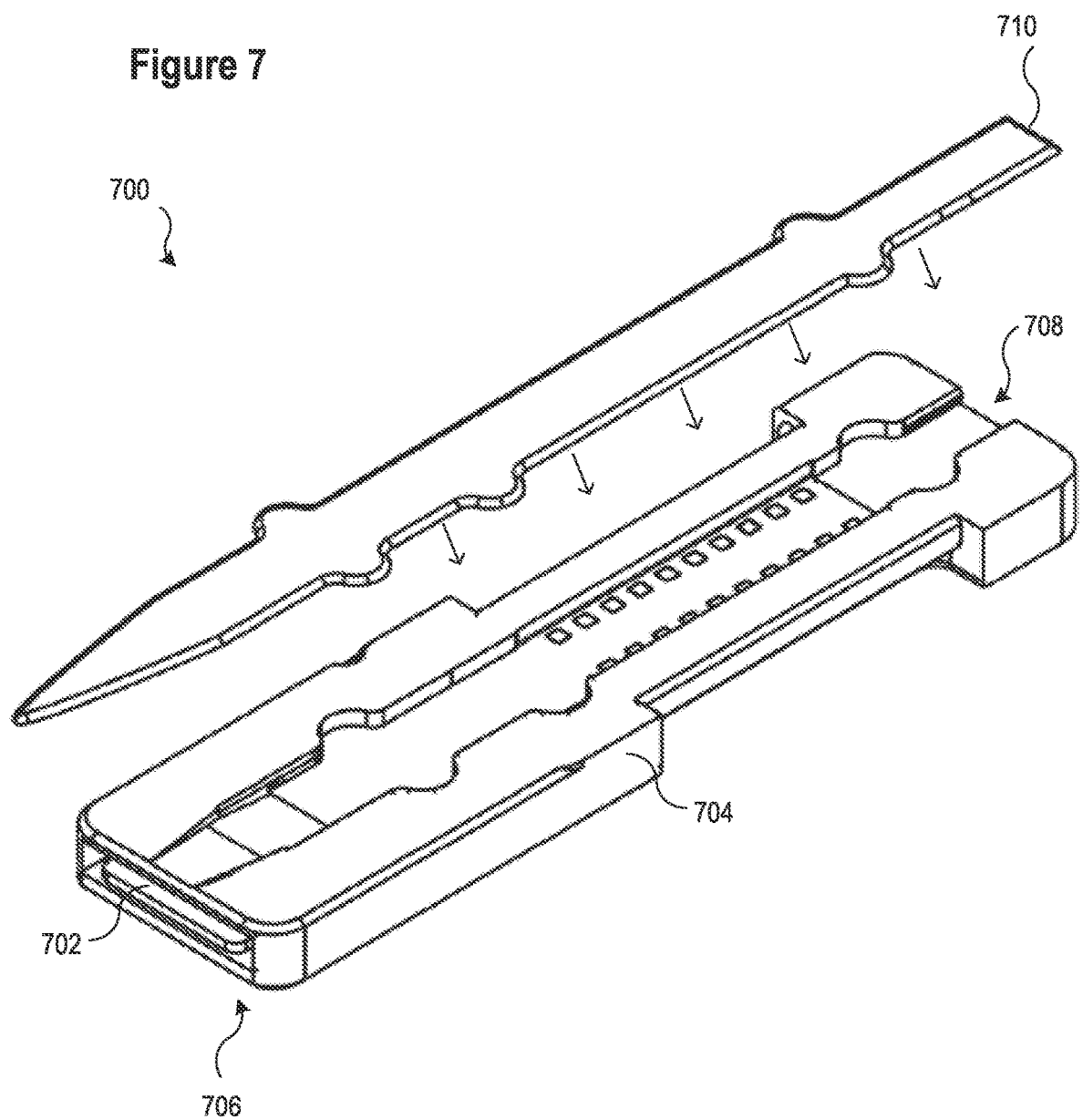
FIG. 7 illustrates a perspective view of an electrical connector body receiving an electrode consistent with embodiments of the present disclosure.

FIG. 7 illustrates a perspective view 700 illustrating insertion of an electrode 710 into an electrical connector body 704 consistent with embodiments of the present disclosure. The electrical connector body 704 receives the electrode 710 within the electrode channel 708. The electrode channel 708 is utilized to allow the electrical connector body 704 to receive the electrode 710 to couple the electrode 710 to the PCB assembly 702. In some embodiments, the electrode channel 708 may correspond to the shape of electrode 710. In some embodiments, the electrode channel 708 and the electrode 710 may be asymmetrical and include multiple features allowing the electrode 710 to be aligned and to remain in place. In the illustrated embodiment, the electrode 710 is received within the electrode channel 708 such that at least one connector pad on the PCB assembly 702 is in electrical contact with at least one electrode pad on the electrode 710.

FIG. 8 illustrates a perspective view of a system 800 wherein the electrode connector system 802 is not coupled to the electrical component 814 consistent with embodiments of the present disclosure. The system 800 may include the electrode connector system 802, the electrical connector body 804, the electrode clamp 806, the electrode 810, the PCB assembly, the coupling component 812, and the electrical component 814. The PCB assembly disposed within the electrode connector system 802 may be in electrical communication with the electrode 810. In the illustrated embodiment, when the electrical component 814 is not coupled to the electrode 810, the coupling component 812 is not engaged. The electrode connector system 802 is illustrated in the closed position; the PCB assembly and the electrode 810 are connected and stabilized. While the electrical component 814 is not coupled to the electrical connector system 800, the electrical component 814 may not be utilized to collect data from the electrode 810. Once the coupling component 812 is engaged, the coupling component 812 couples the electrical connector system 800 to the electrical component 814 and the electrical component 814 may collect data from the electrode 810.

FIG. 9 illustrates a flow chart of a method 900 of electrically connecting an electrode to a PCB assembly consistent with embodiments of the present disclosure. In some embodiments, the electrode is placed on a target area to receive data from neural tissue or muscle tissue. In other embodiments, the electrode may be placed on a target area to stimulate neural tissue or muscle tissue. In some embodiments, an electrode clamp is placed in an open position. In some embodiments, the electrode utilizes two ends: one end for resting on a target area to collect data and stimulate the area, and another end for connecting to the electrical component.

At 902, the electrical connector body may receive the PCB assembly. In some embodiments, a PCB assembly cavity may be disposed within the electrical connector body and may allow the electrical connector body to receive the PCB assembly. At 904, the electrical connector body receives the electrode. In some embodiments, an electrode channel allows the electrical connector body to receive the electrode. At 906, the electrical connector body is coupled to the electrode clamp. In some embodiments, at 906 the electrical connector body contains the PCB assembly and the electrode. In some embodiments, the electrical connector body and the electrode clamp are coupled together by the locking mechanism and the engaging mechanism. At 908, the electrode connection system is coupled to the electrical component. In some embodiments, a coupling component comprises the electrical connector body. In some embodiments, the coupling component may comprise edge contacts. In some embodiments, the PCB assembly allows the coupling component to couple to the electrode connection system. In some embodiments, the coupling component collects data received or stimulated by the electrode.

Many changes may be made to the details of the above-described embodiments without departing from the underlying principles of the invention. The scope of the present invention should, therefore, be determined only by the following claims.

What is claimed is:

1. A system, comprising:
an electrode comprising:
a first plurality of electrically active electrode pads disposed on a first end to receive bioelectrical signals from a target area;
a second plurality of electrically active electrode pads disposed on a second end and in electrical communication with the first plurality of electrically active electrode pads; and
an electrode connection system to electrically connect the electrode to an electrical component, the electrode connection system comprising:
an electrical connector body, comprising:
an electrode channel to receive the electrode; and
an electrode clamp, comprising:
a first portion;
a second portion; and
a hinge to couple the first portion to the second portion and to transition between an open position and a closed position;
wherein the second end of the electrode is secured in the electrode channel in the closed position and removable from the electrode channel in the open position, and the hinge maintains an electrical connection between the second plurality of electrically active electrode pads and the electrical component.

2. The system of claim 1, wherein the electrode connection system further comprises a coupling component to couple the electrode connection system and the electrical component.

3. The system of claim 1, wherein the electrode clamp comprises a snap lock.

4. The system of claim 1, wherein the hinge comprises a hinge protrusion disposed on the first portion of the electrode clamp and a hinge dimple disposed on the second portion of the electrode clamp.

5. The system of claim 1, wherein the electrode connection system comprises a plurality of card edge contacts to couple to the electrical component.

6. The system of claim 1, wherein the electrical connector body further comprises a printed circuit board (PCB) cavity.

7. The system of claim 6, further comprising a plurality of conductors disposed between the electrode channel and the PCB cavity and configured to transmit an electrical signal between the second plurality of electrically active electrode pads and a PCB assembly disposed in the PCB cavity.

8. The system of claim 7, further comprising a plurality of protrusions disposed opposite the plurality of conductors in the electrical connector body and configured to press the plurality of electrically active electrode pads to the plurality of conductors.

9. The system of claim 1, wherein the electrode channel comprises an alignment indicator that corresponds to alignment features on the electrode and configured to align the electrode within the electrode channel.

10. The system of claim 1, wherein the electrode comprises a flexible material.

11. The system of claim 1, wherein the electrical component is configured to transmit bioelectrical signals to the target area.

12. The system of claim 1, wherein the electrical component is configured to record bioelectrical signals from the target area.

* * * * *